United States Patent [19]

Eustis, III et al.

[11] 4,053,636

[45] Oct. 11, 1977

[54] DICHLOROCYCLOPROPYLPHENYL BISBIGUANIDE COMPOUNDS, PROCESSES AND COMPOSITIONS

[75] Inventors: Frederic A. Eustis, III, Portsmouth, Va.; William G. Gorman, East Greenbush; Frederick C. Nachod, Kinderhook, both of N.Y.

[73] Assignee: Sterling Drug Inc., New York, N.Y.

[21] Appl. No.: 689,260

[22] Filed: May 24, 1976

[51] Int. Cl.$^2$ .................. C07C 129/16; A61K 31/155
[52] U.S. Cl. .................................. 424/326; 260/565; 260/501.14; 260/239.1; 260/343.7; 260/501.11; 260/501.12; 260/326.15; 260/296 R; 260/258; 424/280; 424/271; 424/316; 424/263; 424/274; 424/254

[58] Field of Search ................ 260/565, 501.14, 239.1, 260/343.7, 501.11, 501.12, 326.15, 296 R, 258; 424/280, 271, 316, 263, 274, 254, 326

[56] References Cited

U.S. PATENT DOCUMENTS 2,684,924   7/1954   Rose et al. .......................... 260/565

*Primary Examiner*—Gerald A. Schwartz
*Attorney, Agent, or Firm*—Theodore C. Miller; B. Woodrow Wyatt

[57] ABSTRACT

Dichlorocyclopropylphenyl bisbiguanides are prepared by cyanoguanidine-amine condensations. Antimicrobial compositions thereof and their method of use are disclosed.

8 Claims, No Drawings

DICHLOROCYCLOPROPYLPHENYL BISBIGUANIDE COMPOUNDS, PROCESSES AND COMPOSITIONS

BACKGROUND OF THE INVENTION

1. Field of the Invention

This invention relates to dichlorocyclopropylphenyl bisbiguanide compounds, processes for the preparation thereof, compositions thereof, and a process for using the compositions.

2. Description of the Prior Art

U.S. Pat. No. 2,684,924 describes alkylphenyl, alkoxyphenyl, nitrophenyl and halophenyl bisbiguanides, including chlorhexidine. U.S. Pat. No. 3,855,140 describes chlorhexidine compositions.

SUMMARY OF THE INVENTION

In a compound aspect the invention is 1,1'-A-bis-(5-(p-(2,2-dichlorocyclopropyl)phenyl)biguanide) having the structural formula

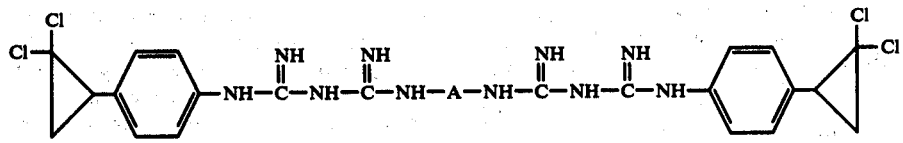

Formula I wherein A is alkylene of two to twelve carbon atoms having the valence bonds attached to different carbon atoms or an acid addition salt thereof.

The dichlorocyclopropylphenyl bisbiguanides of Formula I have antimicrobial activity, particularly against harmful bacteria and fungi, and are useful as antimicrobial agents.

In a process aspect the invention is the process for preparing a dichlorocyclopropylphenyl bisbiguanide of Formula I which comprises condensing p-(2,2-dichlorocyclopropyl)amiline having the structural formula

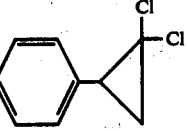

Formula II with 1,1'-A-bis(3-cyanoguanidine) having the structural formula

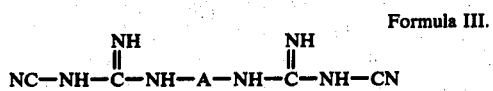

Formula III.

In another process aspect the invention is the process for preparing a dichlorocyclopropylphenyl bisbiguanide of Formula I which comprises condensing 1-(p-(2,2-dichlorocyclopropyl)phenyl)-3-cyanoguanidine having the structural formula

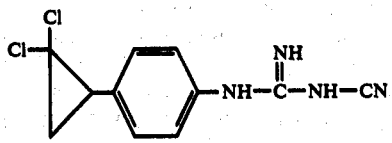

Formula IV with an aklylenediamine having the structural formula $H_2N$-A-$NH_2$ (Formula V).

In a composition aspect the invention is a composition for reducing the number of microbes in liquids, on surfaces or on living tissues which consists essentially of a dichlorocyclopropylphenyl bisbiguanide of Formula I or an acid addition salt thereof and a compatible vehicle.

In still another process aspect the invention is the process for reducing the number of microbes in liquids, on surfaces or on living tissues which comprises applying thereto an antimicrobially effective amount of a dichlororcyclopropylphenyl bisbiguanide of Formula I or an acid addition salt thereof or a composition consisting essentially of a dichlorocyclopropyl bisbiguanide of Formula I or an acid addition salt thereof and a compatible vehicle.

DETAILED DESCRIPTION OF THE INVENTION

Definitions

In Formulas I, III and V A is alkylene having the formula $C_mH_{2m}$ wherein $m$ is an integer from 2 to 12, is bivalent, and has free valence bonds on different carbon atoms. The preferred alkylene is polymethylene having the formula $(CH_2)_m$ wherein the chain is unbranched, but alkylene also includes branched-chain alkylene. Thus, polymethylene is ethylene, trimethylene, tetramethylene, pentamethylene, hexamethylene, heptamethylene, octamethylene, nonamethylene, decamethylene, undecamethylene and dodecamethylene, and branched-chain alkylene is, for example, 1,3-propylene, 1,4-pentylene, 1,10-dodecamethylene, 2-methyl-1,4-butylene and 2-methyl-1,5-pentylene. Hexamethylene is particularly preferred.

The dichlorocyclopropylphenyl bisbiguanides of Formula I are bases and react with organic and inorganic acids to form acid addition salts. Since the bases are bisbases, one molar equivalent of such a base reacts with two molar equivalents of an acid.

Representative acids for the formation of the acid addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid and phosphoric acid. The dihydrochloride and digluconate salts are particularly preferred.

Concerning the compositions compatible means that the antimicrobial effect of the dichlorocyclopropylphenyl bisbiguanide of Formula I is not diminished by the vehicle. The vehicle can include one or more diluents including solvents, surfactants, foam stabilizers, buffering agents, chelating agents, thickeners, builders, abrasives, coloring agents, perfumes, propellants and/or other conventional ingredients. The composition can be in liquid, solid or suspension form, including pressurized sprays, lotions, creams, ointments, gels, bars and powders. An aqueous surfactant vehicle is particularly preferred. The anionic surfactants are believed to be generally incompatible. Cationic and non-ionic surfactants are therefore preferred. A particularly preferred surfactant mixture is a poloxalene-amine oxide mixture, for example, a poloxalene having a molecular weight of 7,700 and a polyoxyethylene content of 70% and dodecyldimethylamine oxide. An intended use of the aqueous surfactant compositions is presurgical antiseptic cleansing of surgeon and/or patient.

Preparation of Final Products and Compositions

The condensations for preparing the dichlorocyclopropylphenyl bisbiguanides of Formula I are preferably carried out using a diluent, heat and an acid addition salt of the dichlorocyclopropylaniline of Formula II or the alkylenediamine of Formula V. The resulting product is the corresponding acid addition salt of the dichlorocyclopropylphenyl bisbiguanide of Formula I, which can be converted into the base and then, if desired, into another addition salt by conventional methods.

The compositions are prepared by conventional methods.

Preparation of Intermediates p-(2,2-Dichlorocyclopropyl)aniline of Formula II is prepared by reduction of p-(2,2-dichlorocyclopropyl)nitrobenzene having the structural formula

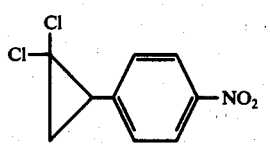

Formula VI, for example, by catalytic hydrogenation, which is prepared by nitration of the known (2,2-dichlorocyclopropyl)benzene having the structural formula

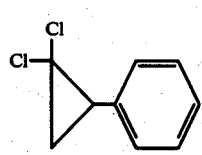

Formula VII.

The nitration also produces the ortho isomer, which is carried through the reduction and separated thereafter.

1-(p-(2,2dichloropropyl)phenyl)-3-cyanoguanidine of Formula IV is prepared by condensing a metal salt of dicyanamide, for example, sodium dicyanamide, with p-(2,2-dichlorocyclopropyl)- aniline of Formula II.

The alkylenediamines of Formula V are known and are converted into the alkylenebiscyanoguanidines of Formula III, which are also known, by condensation with a metal salt of dicyanamide, for example, sodium dicyanamide.

Antimicrobial Testing

The dichlorocyclopropylphenyl bisbiguanides of Formula I and compositions thereof are tested for antimicrobial activity in vitro by conventional serial dilution techniques. For testing the compositions for human skin degerming activity the gloved-hand method of Michaud, McGrath and Goss (Antimicrobial Agents and Chemotherapy, Vol. 2, No. 1, 1972, pp. 8–15) is preferred.

EXAMPLES

The following examples illustrate the invention. Structures of products are inferred from known structures of starting materials and analogous processes and are confirmed, and purity of starting materials and products is determined, by melting temperature, boiling temperature, elemental analysis, infrared spectral analysis, ultraviolet spectral analysis, nuclear magnetic resonance spectral analysis, mass spectral analysis, gas-liquid chromatography and/or thin-layer chromatography.

EXAMPLE 1

Preparation of Intermediates

Nitric acid (25 g.) was added during three hours to a mixture of (2,2-dichlorocyclopropyl)benzene (45 g.), water (13 g.), acetic acid (40 g.) and concentrated sulfuric acid (177 g.) with cooling (to 3–5° C.). The resulting mixture was quenched in a mixture of ice (400 g.) and chloroform (200 g.). The layers were separated and the aqueous layer was washed with chloroform (100 g.). The chloroform layers were combined and washed with aqueous sodium carbonate (5%, 300 ml.). The sodium carbonate layer was backwashed with chloroform (75 g.). The combined chloroform extracts were dried, fitered and concentrated, affording p-(2,2-dichlorocyclopropyl)nitrobenzene mixed with the ortho isomer (57 g.).

A mixture of p-(2,2-dichlorocyclopropyl)nitrobenzene mixed with the ortho isomer (200 g.), ethanol (100 g.) and palladium on carbon (50% wet, 2 g.) was hydrogenated under pressure (50 p.s.i.) with cooling (to 40–50° C.) during one and one-half hours, cooled and stripped of ethanol under vacuum. Toluene (600 g.), concentrated hydrochloric acid (24 g.) and water (440 g.) were added to the residue. The layers were separated and the toluene layer was extracted with a solution of concentrated hydrochloric acid (6 g.) in water (440 g.). The combined aqueous extracts were basified with sodium hydroxide (35%) and extracted with chloroform (300 g. twice). The combined chloroform extracts were dried, treated with charcoal, filtered and concentrated. The dark oil was extracted with hot hexane (500 g. three times). p-(2,2-dichlorocyclopropyl)aniline free of the ortho isomer precipitated from the hexane extracts as a white crystalline solid (67 g., m.r. 58°–60° C.). The hydrochloride salt was formed in benzene with concentrated hydrochloric acid (m.r. 220°–230° C. with decomposition).

A mixture of p-(2,2-dichlorocyclopropyl)aniline (25.1 g.), sodium dicyanamide (12 g.) and water 125 g.) was stirred and heated (at 90°–95° C.) until a complete solution was formed. A solution of concentrated hydrochloric acid (13.3 ml.) in water (15 g.) was added dropwise to the solution during forty-five minutes. The resulting mixture was cooled (at 5° C.) for one hour. The resulting precipitate was washed with hydrochloric acid (10%, 7 ml.) and water (5 ml. three times), dried, slurried with ethanol (50 g. twice) and hot methanol (50 g.), and dried again affording 1-(p-(2,2-dichlorocyclopropyl)-phenyl)-3-cyanoguanidine (9.8 g., m.r. 199°–202° C.).

Preparation of 1,1'-Hexamethylenebis(5-(p-(2,2-dichlorocyclopropyl)-phenyl)biguanide) Hydrochloride and Base A mixture of p-(2,2-dichlorocyclopropyl)aniline hydrochloride (14.2 g.), 1,1'-hexamethylenebis)3-cyanoguanidine) (7.5 g.) and nitrobenzene (100 g.) was stirred and heated (at 140° C.) for four hours, cooled, filtered, and stripped of nitrobenzene with heating (at 60° C.) under vacuum. The residue was slurried in benzene (100 g. twice), affording a brown solid (15.5 g.), part (11 g.) of which was slurried in methanol-water (1:1, 200 g.), affording 1,1'-hexamethylenebis(5-(p-(2,2-dichlorocyclopropyl)phenyl)biguanide) as the dihydrochloride salt, a tan solid (4 g.). The elemental analysis was in agreement with the molecular formula and the infrared, nuclear magnetic resonance and mass spectra were in agreement with the structural formula. Thin layer chromatography showed a small amount of impurity at the origin.

A mixture of 1-(p-(2,2-dichlorocyclopropyl)phenyl)-3-cyanoguanidine (8.3 g.), hexamethylenediamine dihydrochoride (2.8 g.) and nitrobenzene (30 g.) was stirred and heated (at 140°–145° C.) for four hours, cooled and filtered. The filter cake was slurried in a mixture of acetone (75 g.) and acetic acid (7 g.), then hot ethanol (300 g.), affording a light tan solid (2.3 g.), whose thin layer chromatogram showed a substantial amount of 1,1'-hexamethylenebis(5-(p-(2,2-dichlorocyclopropyl)-phenyl)biguanide) but also a substantial amount of impurity.

Treatment of the dihydrochloride salt with sodium hydroxide or other strong base affords 1,1'-hexamethy-lenebis-(5-(p-(2,2-dichlorocyclopropyl)phenyl)biguanide) as the base. In Vitro Antimicrobial Testing of 1,1-Hexamethylenebis(5-(p-(2,2-dichlorocyclopropyl)-phenyl)biguanide) Dihydrochloride

| Organism | Minimum Inhibitory Concentration (mcg./ml.) |
|---|---|
| *Staphylococcus aureus* Smith | 0.5 |
| *Escherichia coli* Vogel | 1.0 |
| *Klebsiella pneumoniae* 39645 | 1.95 |
| *Proteus mirabilis* MGH-1 | 31.3 |
| *Pseudomonas aeruginosa* MGH-2 | 7.8 |
| *Escherichia coli* AB 1932-1 | 1.0 |
| *Escherichia coli* 1100/B22 | 1.0 |
| *Staphylococcus pyogenes* C203 | 0.5 |
| *Aspergillus niger* 16404 | 7.8 |
| *Candida albicans* 10231 | 1.95 |
| *Candida albicans* Wisconsin | 3.9 |
| *Trichophyton mentagraphytes* 9129 | 1.95 |

EXAMPLE 2

1,1'-Hexamethylenebis(5-(p-(2,2-dichlorocyclopropyl)-phenyl)biguanide) Digluconate Aqueous Surfactant Formulation

| Ingredient | Percent by Weight |
|---|---|
| 1,1'-Hexamethylenebis(5-(p-(dichlorocyclopropyl)phenyl)biguanide) base | 2.0 |
| Poloxalene (molecular weight 7,700, 70% polyoxyethylene content) | 25.0 |
| Dodecyldimethylamine oxide (30% in water) | 12.0 |
| Isopropyl alcohol | 5.0 |
| Perfume | q.s. |
| FD&C Red No. 4 | q.s. |
| Gluconic acid to pH 5.7 | q.s. |
| Water q.s. to | 100.0 |

We claim:
1. 1,1'-A-bis(5-(p-(2,2-dichlorocyclopropyl)phenyl)-biguanide) having the structural formula

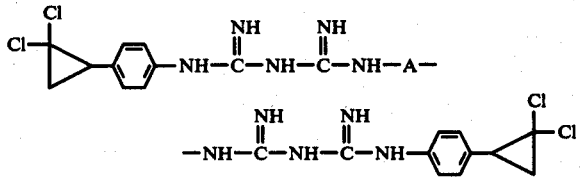

wherein A is alkylene of two to twelve carbon atoms having the valence bonds attached to different carbon atoms or an acid addition salt thereof.
2. 1,1'-Hexamethylenebis(5-(p-(2,2-dichlorocyclopropyl)phenyl)biguanide) or an acid addition salt thereof according to claim 1.
3. A composition for reducing the number of microbes in liquids, on surfaces or on living tissues which consists essentially of an antimicrobially effective amount of 1,1'-A-bis(5-(p-2,2-dichlorocyclopropyl)-phenyl)biguanide) or an acid addition salt thereof and a compatible vehicle wherein A is alkylene of two to twelve carbon atoms having the valence bonds attached to different carbon atoms.
4. A composition wherein A is hexamethylene according to claim 3.
5. A composition wherein the vehicle is an aqueous surfactant according to claim 3.
6. The process for reducing the number of microbes in liquids, on surfaces or on living tissues which comprises applying thereto an antimicrobially effective amount of
   a. 1,1'-A-bis(5-(p-(2,2-dichlorocyclopropyl)phenyl)-biguanide) or an acid addition salt thereof or
   b. a composition consisting essentially of 1,1'-A-bis(5-(p-(2,2-dichlorocyclopropyl)phenyl)biguanide) or an acid addition salt thereof and a compatible vehicle.

wherein A is alkylene of two to twelve carbon atoms having the valence bonds attached to different carbon atoms.
7. The process wherein A is hexamethylene according to claim 6.
8. The process wherein the vehicle is an aqueous surfactant according to claim 7.

* * * * *